United States Patent
Li

(10) Patent No.: US 9,248,208 B2
(45) Date of Patent: Feb. 2, 2016

(54) DEVICE FOR STERILIZING ICE MACHINE USING OZONE GAS FROM ELECTROLYTIC OZONE GENERATOR

(71) Applicants: Mingyung Hsu, Yantai (CN); Gavin Hsu, Yantai (CN)

(72) Inventor: Xin Li, Yantai (CN)

(73) Assignees: Mingyung Hsu, Yantai (CN); Gavin Hsu, Yantai (CN)

( * ) Notice: Subject to any disclaimer, the term of this patent is extended or adjusted under 35 U.S.C. 154(b) by 0 days.

(21) Appl. No.: 14/454,708

(22) Filed: Aug. 7, 2014

(65) Prior Publication Data

US 2015/0050194 A1    Feb. 19, 2015

(30) Foreign Application Priority Data

Aug. 13, 2013  (CN) .......................... 2013 1 0350791

(51) Int. Cl.
  *B01J 19/08*  (2006.01)
  *A61L 2/20*   (2006.01)
  *A23G 9/30*   (2006.01)

(52) U.S. Cl.
  CPC . *A61L 2/202* (2013.01); *A23G 9/30* (2013.01); *A61L 2202/11* (2013.01); *A61L 2202/14* (2013.01)

(58) Field of Classification Search
  CPC . A61L 2/202; A61L 2202/11; A61L 2202/14; A61L 2/183; A61L 2209/212; A61L 2209/213; C25B 1/13; C02F 1/472; C02F 1/78; C02F 1/461; C02F 1/46104; C02F 2201/46; C02F 2201/78; C02F 2209/005
  See application file for complete search history.

(56) References Cited

U.S. PATENT DOCUMENTS 5,098,415 A * 3/1992 Levin ............................ 604/293
2005/0218083 A1* 10/2005 Andrews ....................... 210/748

* cited by examiner

*Primary Examiner* — Xiuyu Tai
(74) *Attorney, Agent, or Firm* — Chun-Ming Shih

(57) ABSTRACT

A device for sterilizing an ice machine using ozone gas from an electrolytic ozone generator includes a pure water tank (2), a pure water refilling device (1), and the electrolytic ozone generator (3). The pure water tank (2) is connected to a gas-feeding solenoid valve (4) and a gas-discharging solenoid valve (5). The gas-discharging solenoid valve (5) is connected to a reducing carbon tank (6), which is connected to a vent (10). The gas-feeding solenoid valve (4) is connected to a tee pipe (11-4) of the ice machine (11). The tee pipe (11-4) is connected to a water pump (11-2) in an ice-machine water tank (11-1) and an ice-machine evaporator (11-3) through loop piping. A controlling circuit board (7) is connected to power source (8), and further connected to the electrolytic ozone generator (3), the gas-feeding solenoid valve (4), the gas-discharging solenoid valve (5), and a motherboard (11-6).

3 Claims, 3 Drawing Sheets

US 9,248,208 B2

DEVICE FOR STERILIZING ICE MACHINE USING OZONE GAS FROM ELECTROLYTIC OZONE GENERATOR

BACKGROUND OF THE INVENTION

1. Technical Field

The present invention relates to ozone generators, and more particularly, to a device for sterilizing an ice machine using ozone gas from an electrolytic ozone generator.

2. Description of Related Art

It is known that ice machines tend to be contaminated by microorganisms such as bacteria, saccharomycete, fungus and moulds. Tap water that has the residual chlorine filtered out is particular a great medium for bacteria to propagate. It is often reported that some famous fast-food stores provide ice tested as containing excessive bacteria. This is not only a serious threat to consumers' human health, but also a disservice to businesses' reputation. Ozone is known as effective, wide-spectrum, and residuum-free sterilization technology and is applicable for this use. Currently, there are some ice machines using ozone for sterilization. However, most of them generate ozone by using the high-voltage discharge method to ionize the air and this way inevitably incurs the production of nitrogen oxides that are believed responsible for certain cancers. On the other hand, in some other existing ice machine that use electrolytic ozone-water mixing devices, since the water inlet of such an ice machine is equipped with a throttle-type solenoid valve, its operation required a high water pressure, and this makes the device complex.

SUMMARY OF THE INVENTION

In view of the shortcomings of the prior art, the objective of the present invention is to provide a device for sterilizing an ice machine using ozone gas from an electrolytic ozone generator that is structurally simple utility, economical, providing excellent effects of sterilization and bacteriostasis.

For achieving the objective of the present invention, a device for sterilizing an ice machine using ozone gas from an electrolytic ozone generator as disclosed comprises a pure water tank connected to a pure water refilling device, and the electrolytic ozone generator connected to a sewage draining exit, wherein the device is characterized in: the pure water tank having an ozone outlet thereof connected to a gas-feeding solenoid valve and a gas-discharging solenoid valve, respectively; the gas-discharging solenoid valve having a gas outlet thereof connected to a reducing carbon tank; the reducing carbon tank being connected to a vent; the gas-feeding solenoid valve having a gas outlet thereof connected to a tee pipe of the ice machine through piping; the tee pipe being connected to a water pump in an ice-machine water tank and an ice-machine evaporator through loop piping, respectively; a controlling circuit board being connected to a power source and further connected to the electrolytic ozone generator, the gas-feeding solenoid valve, and the gas-discharging solenoid valve, respectively; the controlling circuit board being connected to a motherboard of the ice machine through an ice-machine controlling signal line.

For further achieving the objective of the present invention, the controlling circuit board comprises a DC/DC converting power source connected to an MCU controller unit and an ice-machine signal-processing unit; the MCU controller unit being connected to an ozone-generator power-source controlling unit, a solenoid-valve controlling unit, and the ice-machine signal-processing unit, respectively; a power source being connected to the DC/DC converting power source, the ozone-generator power-source controlling unit, and the solenoid valve controlling unit, respectively; the ozone-generator power-source controlling unit being connected to the electrolytic ozone generator; the solenoid valve controlling unit being connected to the gas-feeding solenoid valve and the gas-discharging solenoid valve, respectively; and the ice-machine signal-processing unit being connected to the ice machine controlling signal line.

For further achieving the objective of the present invention, the ice-machine signal-processing unit comprises a wire terminal L1 having a first pin thereof connected to a capacitor C1; the capacitor C1 being connected to a resistor R1 and a capacitor C2; the capacitor C2 being connected to a second pin of the wire terminal L1; the resistor R1 being connected to an anode of the diode D1; a cathode of the diode D1 being connected to an opticalcoupler U1, a cathode of the diode D2 and a resistor R2; the opticalcoupler U1 and an anode of a diode D2 being connected to wire terminal L1; the resistor R2 being connected to a third pin of the wire terminal L1; the second pin of the wire terminal L1 being connected to a fourth pin of the wire terminal L1; the opticalcoupler U1 being connected to a resistor R3; the resistor R3 being connected to a power source VCC; the opticalcoupler U1 being ground, wherein the first and second pins of the wire terminal L1 are connected to an AC signal line of an ice-machine controlling-signal line, or the third and fourth pins of the wire terminal L1 are connected to a signal line of the ice-machine controlling-signal line, in which the first and second pins of the wire terminal L1 and the third and fourth pins of the wire terminal L1 are not such connected simultaneously; and the opticalcoupler U1 being connected to the MCU controller unit.

As compared to the prior art, the present invention provides the following benefits. The present invention uses the electrolytic ozone generator generates ozone gas by electrolyzing pure water, free from deleterious gas such as nitrogen oxides. With the generated ozone gas being delivered into the ice machine directly, the disclosed device is simple in terms of structure and economic in terms of cost. The ozone gas, after entering the ice machine, one part thereof is mixed with water to form ozone water that disinfects iced water, water tanks and where the ozone water flow through, while the rest of the ozone gas escapes to the air and form an ozone-containing atmosphere around the water tank and the evaporator of the ice machine, so as to provide bacteriostasis inside of the ice machine.

DETAILED DESCRIPTION OF THE INVENTION

For further illustrating the means and functions by which the present invention achieves the certain objectives, the following description, in conjunction with the accompanying drawings and preferred embodiments, is set forth as below to illustrate the implement, structure, features and effects of the subject matter of the present invention.

Figure 1:
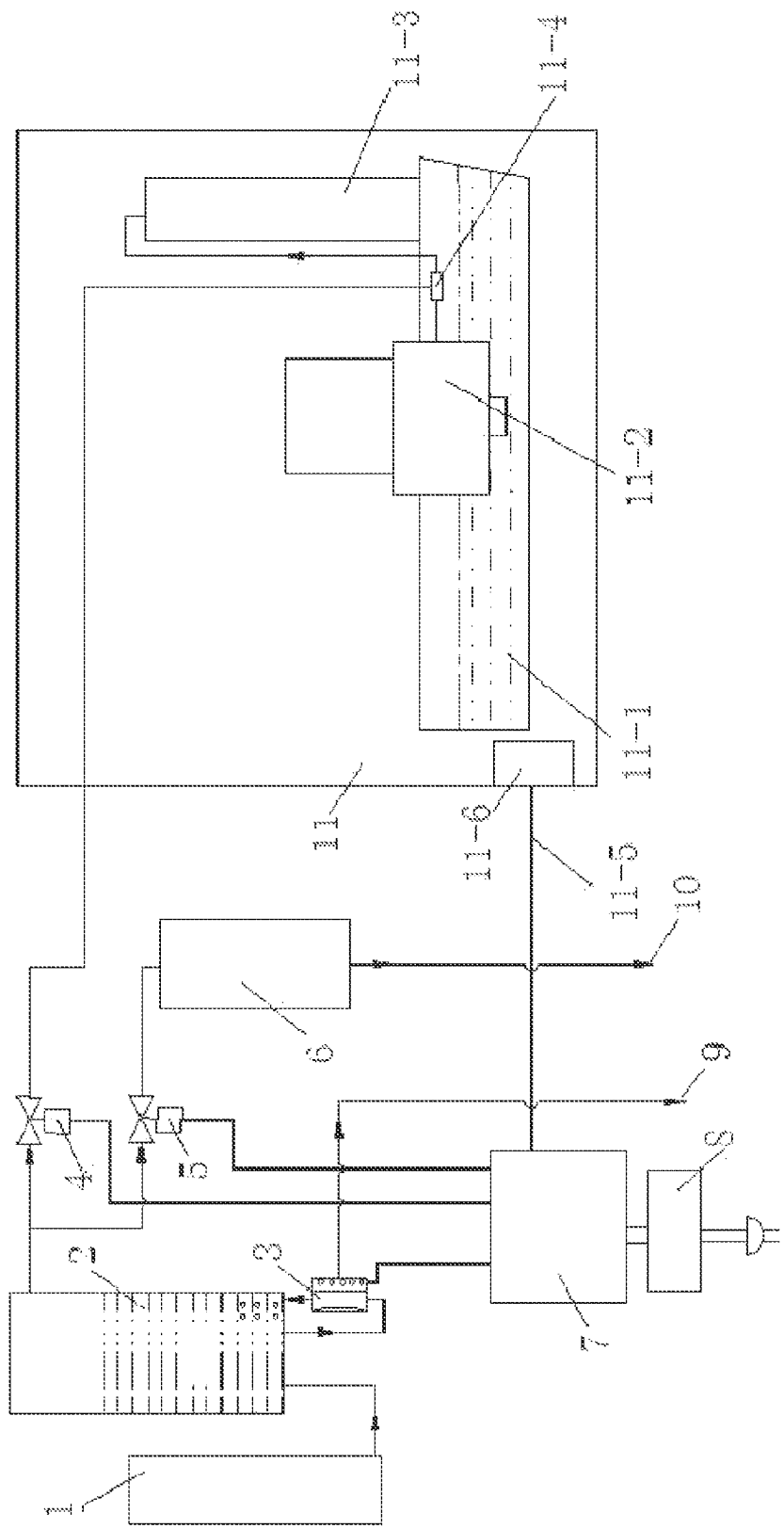
FIG. 1 is a schematic drawing showing one mode for embodying the present invention.
Figure 2:
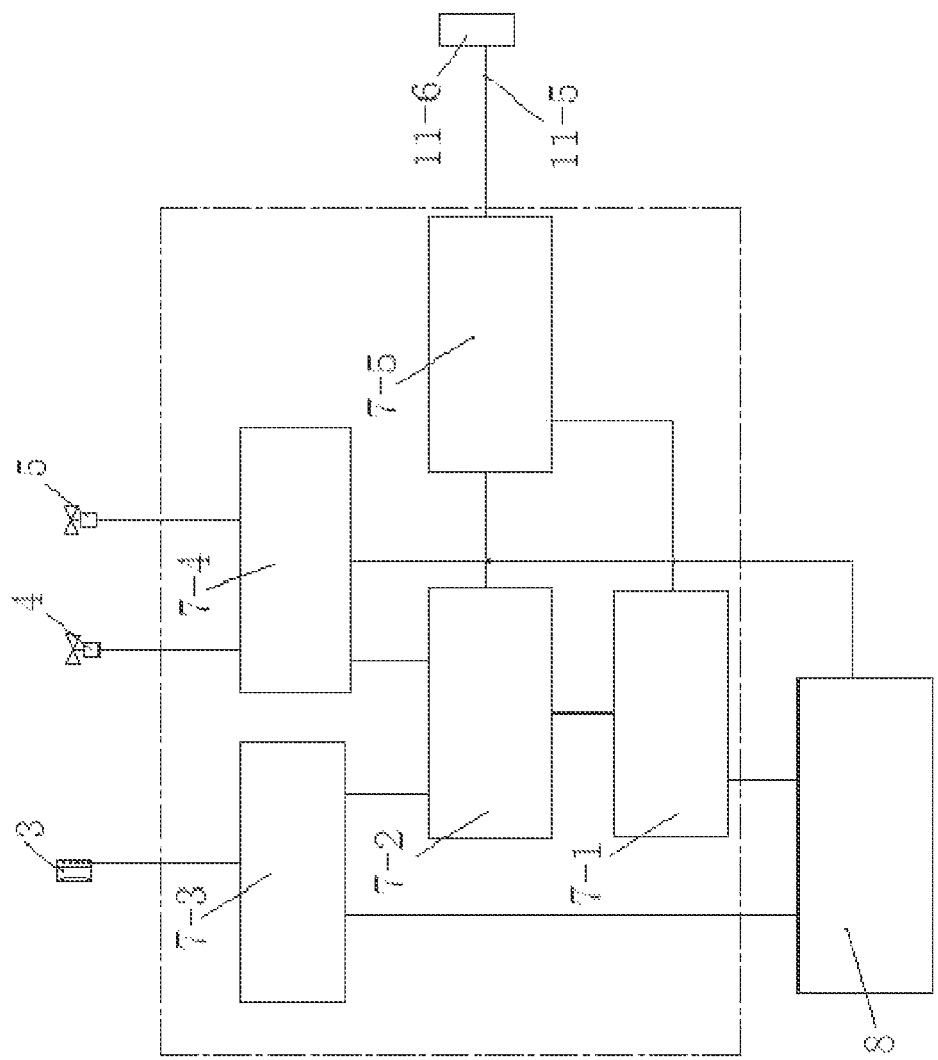
FIG. 2 is a circuit block diagram of a controlling circuit board according to the present invention.
Figure 3:
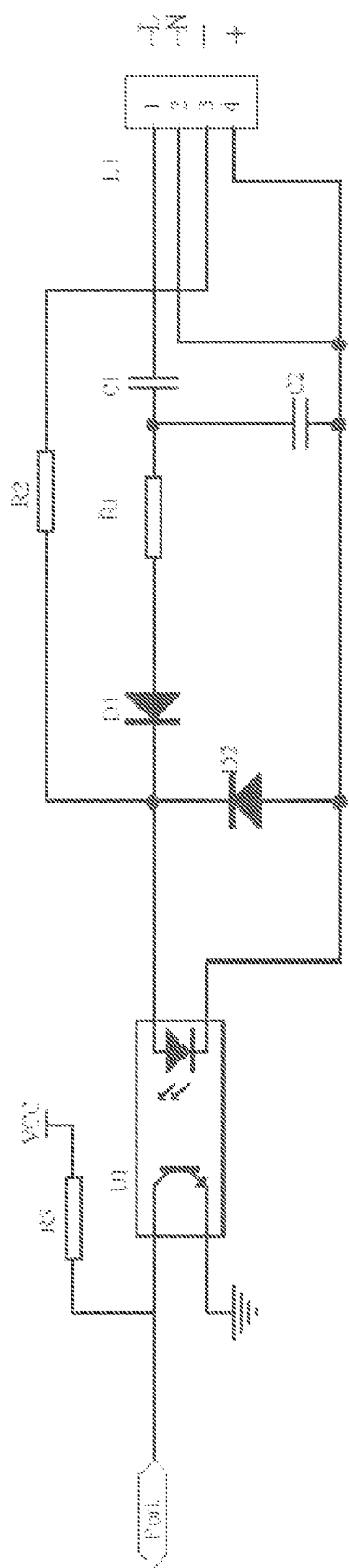
FIG. 3 is a circuit block diagram of the ice-machine signal-processing unit as shown in FIG. 2.

According to one embodiment of the present invention, a device for sterilizing an ice machine using ozone gas from an electrolytic ozone generator (referring to FIG. 1, FIG. 2 and FIG. 3) comprises a pure water tank 2 that is connected to a pure-water refilling device 1. The pure water tank 2 has its gas inlet and water outlet connected to the gas outlet at the anode and a water inlet of the electrolytic ozone generator 3, respectively. The electrolytic ozone generator 3 has a gas outlet at its cathode connected to a sewage draining exit 9. An ozone gas outlet at the upper end of the pure water tank 2 is connected to the gas-feeding solenoid valve 4 and gas-discharging solenoid valve 5, respectively. The gas-discharging solenoid valve 5 has its gas outlet connected to a reducing carbon tank 6. The reducing carbon tank 6 is connected to a vent 10. The gas-feeding solenoid valve 4 has its gas outlet connected to a tee pipe 11-4 of an ice machine 11 through piping. The tee pipe 11-4 is connected to a water pump 11-2 in an ice-machine water tank 11-1 and an ice-machine evaporator 11-3 through loop piping, respectively. The ice machine is an existing ice machine and not the subject of the present invention, so the description and drawing illustrating the present embodiment are only made to what forms the features of the present invention.

A controlling circuit board 7 is connected to a power source 8. The controlling circuit board 7 is connected to the electrolytic ozone generator 3, the gas-feeding solenoid valve 4, and the gas-discharging solenoid valve 5, respectively. The controlling circuit board 7 is connected to a motherboard 11-6 of the ice machine through an ice-machine controlling-signal line 11-5.

The controlling circuit board 7 (referring to FIG. 2) comprises a DC/DC converting power source 7-1. The converting power source 7-1 is connected to an MCU controller unit 7-2 and an ice-machine signal-processing unit 7-5. The MCU controller unit 7-2 is connected to an ozone-generator power-source controlling unit 7-3, a solenoid valve controlling unit 7-4, and an ice-machine signal-processing unit 7-5, respectively. The power source 8 is connected to the DC/DC converting power source 7-1, the ozone-generator power-source controlling unit 7-3, and the solenoid valve controlling unit 7-4, respectively. The ozone-generator power-source controlling unit 7-3 is connected to the electrolytic ozone generator 3. The solenoid valve controlling unit 7-4 is connected to the gas-feeding solenoid valve 4 and the gas-discharging solenoid valve 5, respectively. The ice-machine signal-processing unit 7-5 is connected to the ice machine controlling signal line 11-5. The ice machine controlling signal line 11-5 may be the controlling signal line on an ice-machine loop pump 11-2, or may be the signal line provided by the motherboard 11-6 of the ice machine.

The ice-machine signal-processing unit 7-5 (referring to FIG. 3) comprises a wire terminal L1. The wire terminal L1 has its first pin connected to a capacitor C1. The capacitor C1 is connected to a resistor R1 and a capacitor C2. The capacitor C2 and a second pin of L1 are connected. The resistor R1 is connected to an anode of a diode D1. The diode D1 has its cathode is connected to opticalcoupler U1, a cathode of a diode D2 and a resistor R2. The opticalcoupler U1, an anode of the diode D2 and L1 are connected. The resistor R2 is connected to a third pin of L1. L1 has its second pin connected to a fourth pin thereof. The opticalcoupler U1 is connected to a resistor R3. The resistor R3 is connected to a power source VCC (at the power source's anode). U1 is grounded (at the power source's cathode). The wire terminal L1 has its first and second pins connected to an AC signal (ice-machine solenoid-valve controlling signal) line of an ice-machine controlling-signal line 10-4. Alternatively, the third and fourth pins of L1 are connected to a DC signal (ice-machine controlling-board controlling signal) line of the ice machine controlling signal line 10-4. It is to be noted that the foregoing connection of the first and second pins of the wire terminal L1 and of L1's third and fourth pins shall be only implemented alternatively but never simultaneously. The opticalcoupler U1 is connected to the MCU controller unit 7-2.

When the ice-machine AC signal (the controlling signal for the ice-machine loop pump 11-2) line is connected to the first and second pins of L1, and there is an AC signal, through the step-down network formed by the capacitor C1 and the capacitor C2, a low-voltage alternating current is generated at the resistor R1, which is limited by the resistor R1 and rectified by the diode D1, and then power the opticalcoupler U1, so that the phototransistor of the opticalcoupler U1 is on, and the opticalcoupler U1 comes to a low level. The purpose of the diode D2 is to protect the opticalcoupler when the Ac current reverses. When the MCU controller unit 7-2 detects that the opticalcoupler U1 is at the low level, it controls the ozone-generator power-source controlling unit 7-3 to activate the generator, and controls the solenoid-valve controlling unit 7-4 to open the gas-feeding solenoid valve 4 and close the gas-discharging solenoid valve 5, so as to provide ozone gas to the ice machine. When there is no AC signal passing through the step-down network formed by the capacitor C1 and the capacitor C2, there is no low-voltage AC at the resistor R1 to be limited by the resistor R1 and rectified by the diode D1. The opticalcoupler U1 does not illuminate. The phototransistor of the opticalcoupler U1 stops. Then the resistor R3 pulls the opticalcoupler U1 up to a high level. At this time, the MCU controller unit 7-2 detects the high level of the opticalcoupler U1 and controls the ozone-generator power-source controlling unit 7-3 to deactivate the generator, and controls the solenoid valve controlling unit 7-4 to close the gas-feeding solenoid valve 4 and open the gas-discharging solenoid valve 5, thereby stopping delivering ozone gas to the ice machine.

In the alternative case where the ice-machine DC signal (ice-machine controlling-board controlling signal) line is connected to the third and fourth pins of L1, similar to the case described previously, when there is a DC signal, it is limited by the resistor R2 to light up the opticalcoupler U1, thereby turning on the phototransistor of the opticalcoupler U1. The opticalcoupler U1 therefore comes to a low level. When there is no DC signal limited by the resistor R2, the opticalcoupler U1 does not illuminate and the phototransistor of the opticalcoupler U1 is stopped. Then the resistor R3 pulls the opticalcoupler U1 up to a high level. The control method is consistent to that described above.

When there is not sufficient pure water in the pure water tank 2, the pure-water refilling device 1 refills the pure water tank 2 with pure water. The power source 8 powers the electrolytic ozone generator 3 through the controlling circuit board 7. The electrolytic ozone generator 3 generates ozone gas at its anode. The generated ozone gas then enters the pure water tank 2, and goes to the gas-feeding solenoid valve 4 and the gas-discharging solenoid valve 5 through the upper-end ozone gas outlet. When the controlling circuit board 7 gets the information that the ice machine 11 needs ozone gas through the ice-machine controlling-signal line 11-5, the controlling circuit board 7 opens the gas-feeding solenoid valve 4 and closes the gas-discharging solenoid valve 5. The ice-machine loop pump 11-2 draws the water in the ice-machine water tank 11-1 into the loop piping, and the ozone gas enters the loop piping of the ice machine 11 to get mixed with the loop water so as to form ozone water. The ozone water is frozen into ice while passing through the ice-machine evaporator 11-3. When there is no need for ozone gas, the controlling circuit board 7 closes the gas-feeding solenoid valve 4 and opens the gas-discharging solenoid valve 5, so that the ozone gas enters the reducing carbon tank 6 through piping and reduces into oxygen that is discharged via the vent 10. The rest of the ozone gas escapes into the air, so as to form an ozone-containing atmosphere around the ice machine's water tank and evaporator, thereby providing bacteriostasis inside the ice machine.

The present invention has been described with reference to the preferred embodiments and it is understood that the embodiments are not intended to limit the scope of the present invention. Moreover, as the contents disclosed herein should be readily understood and can be implemented by a person skilled in the art, all equivalent changes or modifications which do not depart from the concept of the present invention should be encompassed by the appended claims.

What is claimed is:

1. A device for sterilizing an ice machine using ozone gas from an electrolytic ozone generator, the device comprising a pure water tank (2) connected to a pure water refilling device (1), and the electrolytic ozone generator (3) connected to a sewage draining exit (9), wherein the device is characterized in: the pure water tank (2) having an ozone outlet thereof connected to a gas-feeding solenoid valve (4) and to a gas-discharging solenoid valve (5), respectively; the gas-discharging solenoid valve (5) having a gas outlet thereof connected to a reducing carbon tank (6); the reducing carbon tank (6) being connected to a vent (10); the gas-feeding solenoid valve (4) having a gas outlet thereof connected to a tee pipe (11-4) of the ice machine (11) through piping; the tee pipe (11-4) being connected to a water pump (11-2) in an ice-machine water tank (11-1) and an ice-machine evaporator (11-3) through loop piping, respectively; a controlling circuit board (7) being connected to a power source (8) and further connected to the electrolytic ozone generator (3), to the gas-feeding solenoid valve (4), and to the gas-discharging solenoid valve (5), respectively; the controlling circuit board (7) being connected to a motherboard (11-6) of the ice machine (11) through an ice-machine controlling signal line (11-5).

2. The device of claim 1, wherein the controlling circuit board (7) comprises a DC/DC converting power source (7-1) connected to an MCU controller unit (7-2) and to an ice-machine signal-processing unit (7-5); the MCU controller unit (7-2) being connected to an ozone-generator power-source controlling unit (7-3), to a solenoid-valve controlling unit (7-4), and to the ice-machine signal-processing unit (7-5), respectively; a power source (8) being connected to the DC/DC converting power source (7-1), to the ozone-generator power-source controlling unit (7-3), and to the solenoid valve controlling unit (7-4), respectively; the ozone-generator power-source controlling unit (7-3) being connected to the electrolytic ozone generator (3); the solenoid valve controlling unit (7-4) being connected to the gas-feeding solenoid valve (4) and to the gas-discharging solenoid valve (5), respectively; and the ice-machine signal-processing unit (7-5) being connected to the ice machine controlling signal line (11-5).

3. The device of claim 2, wherein the ice-machine signal-processing unit (7-5) comprises a wire terminal (L1) having a first pin thereof connected to a first capacitor (C1); the first capacitor (C1) being connected to a first resistor (R1) and to a second capacitor (C2); the second capacitor (C2) being connected to a second pin of the wire terminal (L1); the first resistor (R1) being connected to an anode of a first diode (D1); a cathode of the first diode (D1) being connected to an opticalcoupler (U1), to a cathode of a second diode (D2) and to a second resistor (R2); the opticalcoupler (U1) and an anode of a second diode (D2) being connected to the wire terminal (L1); the second resistor (R2) being connected to a third pin of the wire terminal (L1); the second pin of the wire terminal (L1) being connected to a fourth pin of the wire terminal (L1); the opticalcoupler (U1) being connected to a third resistor (R3); the third resistor (R3) being connected to the power source; the opticalcoupler (U1) being ground, wherein the first and second pins of the wire terminal (L1) are connected to an AC signal line of an ice-machine controlling-signal line (10-4), or the third and fourth pins of the wire terminal (L1) are connected to a DC signal line of the ice-machine controlling-signal line (10-4), in which the first and second pins of the wire terminal (L1) and the third and fourth pins of the wire terminal (L1) are not such connected simultaneously; and the opticalcoupler (U1) being connected to the MCU controller unit (7-2).

\* \* \* \* \*